United States Patent
Kagan et al.

[11] Patent Number: 5,311,866
[45] Date of Patent: May 17, 1994

[54] HEART MAPPING CATHETER

[75] Inventors: Jonathan Kagan, Minneapolis; Graydon E. Beatty; Jeffrey R. Budd, both of St. Paul, all of Minn.

[73] Assignee: Endocardial Therapeutics, Inc., St. Paul, Minn.

[21] Appl. No.: 949,690

[22] Filed: Sep. 23, 1992

[51] Int. Cl.$^5$ .............................. A61B 5/04
[52] U.S. Cl. ........................ 128/642; 607/122; 29/872
[58] Field of Search ............ 128/639, 641–642, 128/783–786, 419 P; 604/96, 164; 29/868, 872–873; 607/115–116, 119, 122–123, 125–128

[56] References Cited

U.S. PATENT DOCUMENTS

| | | | |
|---|---|---|---|
| 4,304,239 | 12/1981 | Perlin | 128/642 |
| 4,444,195 | 4/1984 | Gold | 128/642 |
| 4,522,212 | 6/1985 | Gelinas et al. | 128/642 |
| 4,559,951 | 12/1985 | Dahl et al. | 128/642 |
| 4,572,186 | 2/1986 | Gould et al. | 128/341 |
| 4,573,473 | 3/1986 | Hess | 128/642 |
| 4,628,937 | 12/1986 | Hess et al. | 128/642 |
| 4,649,924 | 3/1987 | Taccardi | 128/642 |
| 4,699,147 | 10/1987 | Chilson et al. | 128/642 |
| 4,706,670 | 11/1987 | Andersen et al. | |
| 4,777,955 | 10/1988 | Brayton et al. | 128/642 |
| 4,922,912 | 5/1990 | Watanabe | 128/642 |
| 4,940,064 | 7/1990 | Desai | |
| 4,945,342 | 7/1990 | Steinemann | |
| 5,005,587 | 4/1991 | Scott | |
| 5,025,786 | 6/1991 | Siegel | 128/642 |
| 5,156,151 | 10/1992 | Imran | 128/642 |

FOREIGN PATENT DOCUMENTS

0499491A2 8/1992 European Pat. Off. ........ A61N 1/05

Primary Examiner—Angela D. Sykes
Attorney, Agent, or Firm—Merchant, Gould, Smith, Edell, Welter & Schmidt

[57] ABSTRACT

A mapping catheter assembly 10 including a flexible lead body 12 and a deformable lead body 14. A lumen 22 is provided to accept a reference catheter 18 which includes a distal tip electrode assembly 29. In use an array 16 of electrode sites are deformed into a spherical shape after the assembly is placed in a heart chamber. The reference electrode assembly 29 is advanced into contact with the heart wall to provide calibration information for the array 16.

12 Claims, 4 Drawing Sheets

HEART MAPPING CATHETER

CROSS-REFERENCE TO RELATED U.S. CASES

The present application is related to copending U.S. patent application Ser. No. 07/950,448, filed, Sep. 23, 1992, disclosing a method of using the heart mapping catheter apparatus disclosed herein.

TECHNICAL FIELD

The present invention relates generally to endocardial catheters which can be used to map the electrical activity of the heart, and more particularly to a multiple electrode catheter and its method of manufacture.

BACKGROUND ART

Cardiac arrhythmias can be treated pharmacologically, surgically, or by the implantation of a medical device. In the case of a tachycardia it is now common to perform endocardial mapping to determine the origin and mechanism of the arrythmia prior to selecting a therapeutic approach. Endocardial mapping can also be used to monitor or assess the efficacy of a therapy once selected and delivered.

Traditionally endocardial mapping techniques involve the introduction of one or more catheters into the patient, advancing the catheters through a blood vessel and placing the catheters in a heart chamber. Once located in the heart, the electrode or electrodes of the catheters are pressed against the endocardial surface to record the electrical potential of the cardiac tissue at that electrode site. Single electrode contact systems are tedious to use but they do not interfere with the normal blood flow through the heart. Multiple electrode contact systems are also available to permit simultaneous mapping of potentials from several electrode sites. However some of these systems block blood flow through the heart. Multiple electrode systems which do not interfere with the blood flow, and which do not contact the surface of the heart are also known, although these systems do not permit a high resolution map of the endocardial surface.

U.S. Pat. No. 4,649,924 to Taccardi teaches a catheter which is inserted into the heart chamber. The distal end of this catheter is formed into an elliptical shape which is much smaller than the heart chamber. The multiple electrodes on the surface of this ellipsoid may be used to detect the electrical potential produced by the area of the endocardial surface proximate each individual electrode. Accurate measurements require that the electrodes do not touch the endocardial surface. This type of catheter floats freely in the heart chamber but will typically touch the walls of the beating heart. The constant motion of the catheter and contact with the walls frustrates accurate measurement of the cardiac potentials. Therefore these prior non-contact mapping and in-contact mapping catheters compromise the accuracy of the resultant map with the ease of use. Therefore there is a need for a catheter which can be used to develop an accurate representation of the electrical activity of the heart.

SUMMARY DISCLOSURE OF THE INVENTION

The mapping catheter assembly 10 includes a flexible lead body 12 connected to a deformable distal lead body 14. The deformable distal lead body 14 can be formed into a stable space filling geometric shape after introduction into the heart cavity 20. This deformable distal lead body 14 includes an electrode array 16 defining a number of electrode sites. The mapping catheter assembly 10 also includes a reference electrode preferably placed on a reference catheter 18 which passes through a central lumen 22 formed in the flexible lead body 12 and the distal lead body 14. The reference catheter assembly 18 has a distal tip electrode assembly 29 which may be used to probe the heart wall. This distal contact electrode assembly 29 provides a surface or subsurface electrical reference for calibration. The physical length of the reference catheter 18 taken with the position of the electrode array 16 together provide a reference which may be used to calibrate the electrode array 16. The reference catheter 18 also stabilizes the position of the electrode array 16 which is desirable.

These structural elements provide a mapping catheter assembly which can be readily positioned within the heart and used to acquire highly accurate information concerning the electrical activity of the heart from a first set of preferably non-contact electrode sites and/or a second set of in-contact electrode sites.

BRIEF DESCRIPTION OF THE DRAWING

An illustrative example of the invention is shown in the drawing. Throughout the various figures of the drawing identical numerals refer to identical structure.

DETAILED DISCLOSURE OF THE INVENTION

Figure 1:
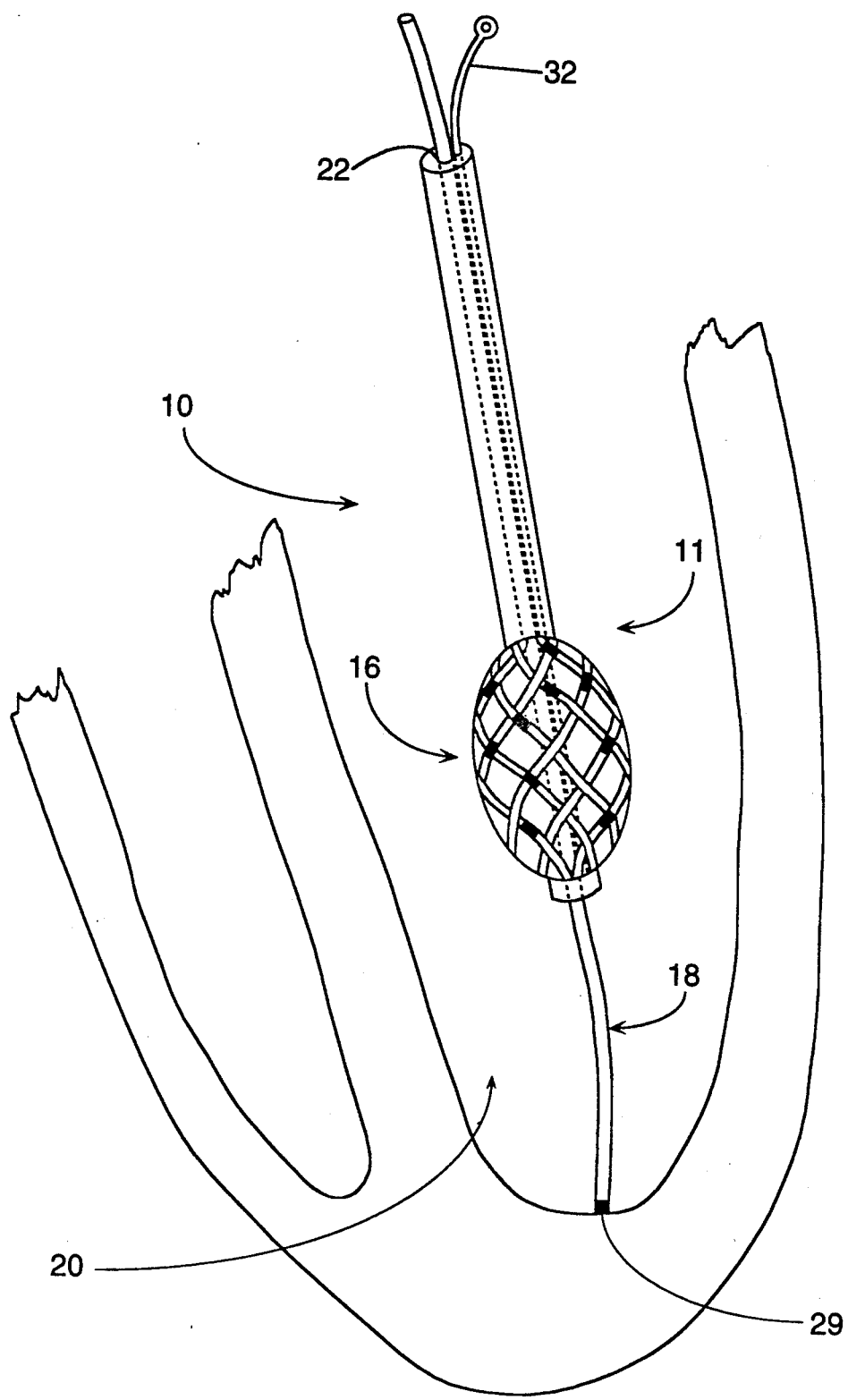
FIG. 1 is a view of the catheter assembly placed in an endocardial cavity.

FIG. 1 shows a portion of the mapping catheter assembly 10 placed into a heart chamber 20. The mapping catheter assembly 10 includes a reference catheter 18 and an array catheter 11. In FIG. 1 the array catheter 11 has been expanded through the use of a stylet 32 to place the electrode array 16 into a stable and reproducible geometric shape. The reference catheter 18 has been passed through the lumen 22 of the array catheter 11 to place a distal tip electrode assembly 29 into position against an endocardial surface. In use, the reference catheter 18 provides a mechanical location reference for the position of the electrode array 16, and the tip electrode assembly 29 provides an electrical potential reference at or in the heart wall for the mapping process.

Although the structures of FIG. 1 are preferred there are several alternatives within the scope of the invention. The principle objective of the preferred form of the catheter system is to reliably place a known collection of electrode sites away from the endocardial surface, and one or more electrode sites into contact with the endocardium. The array catheter is an illustrative structure for placing at least some of the electrode sites away from the endocardial surface. The array catheter itself can be designed to mechanically position one or more electrode sites on the endocardial surface. The reference catheter is a preferred structure for carrying one or more electrode sites and may be used to place these electrode sites into intimate contact with the endocardial surface.

It should be understood that the reference catheter could be replaced with a fixed extension of the array catheter and used to push a segment of the array into the endocardial surface. In this embodiment the spherical array maintains the other electrodes out of contact with the endocardial surface.

Figure 2:
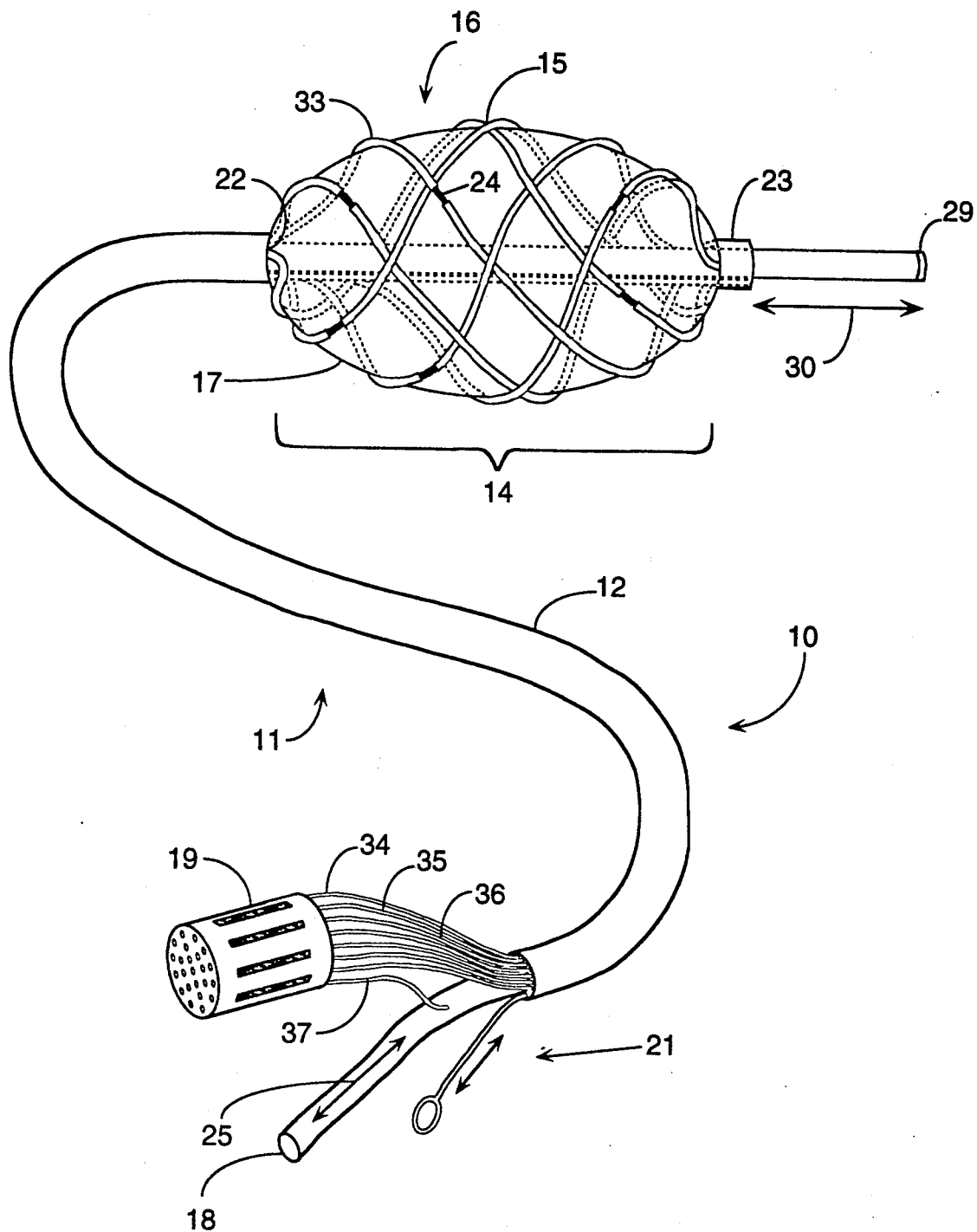
FIG. 2 is a schematic view of the catheter assembly.

FIG. 2 shows the preferred construction of the mapping catheter assembly 10 in exaggerated scale to clarify details o construction. In general, the array catheter 11 includes a flexible lead body 12 coupled to a deformable lead body 14. The deformable lead body 14 is preferably a braid 15 of insulated wires, several of which are shown as wire 33, wire 34, wire 35 and wire 36. An individual wire such as 33 may be traced in the figure from the electrical connection 19 at the proximal end 21 of the flexible lead body 12 through the flexible lead body 12 to the distal braid ring 23 located on the deformable lead body 14. At a predetermined location in the deformable lead body 14 the insulation has been selectively removed from this wire 33 to form a representative electrode site 24. Each of the several wires in the braid 15 may potentially be used to form an electrode site Preferably all of the typically twenty-four to sixty-four wires in the braid 15 are used to form electrode sites. Wires not used as electrode sites provide mechanical support for the electrode array 16. In general, the electrode sites will be located equidistant from a center defined at the center of the spherical array. Other geometrical shapes are possible including ellipsoidal and the like. However, it is generally desirable to have the electrode sites positioned in a spherical array.

The proximal end 21 of the mapping catheter assembly 10 has suitable electrical connection 19 for the individual wires connected to the various electrode sites. Similarly the proximal connector 19 can have a suitable electrical connection for the distal tip electrode assembly 29 of the reference catheter 18 or the reference catheter 18 can use a separate connector. The distance 30 between the electrode array 16 and the distal tip assembly 29 electrode ca preferentially be varied by sliding the reference catheter through the lumen 22, as shown by motion arrow 25. This distance 30 may be "read" at the proximal end 21 by noting the relative position of the end of the lead body 12 and the proximal end of the reference catheter 18.

Figure 3:
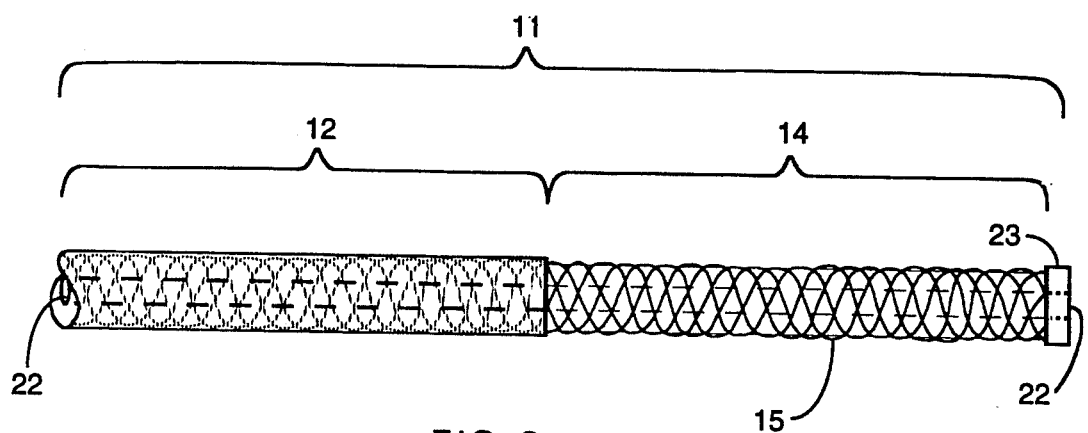
FIG. 3 is a view of the mapping catheter with the deformable lead body in the collapsed position.

FIG. 3 is a view of the mapping catheter with the deformable lead body 14 in the collapsed position.

Figure 4:
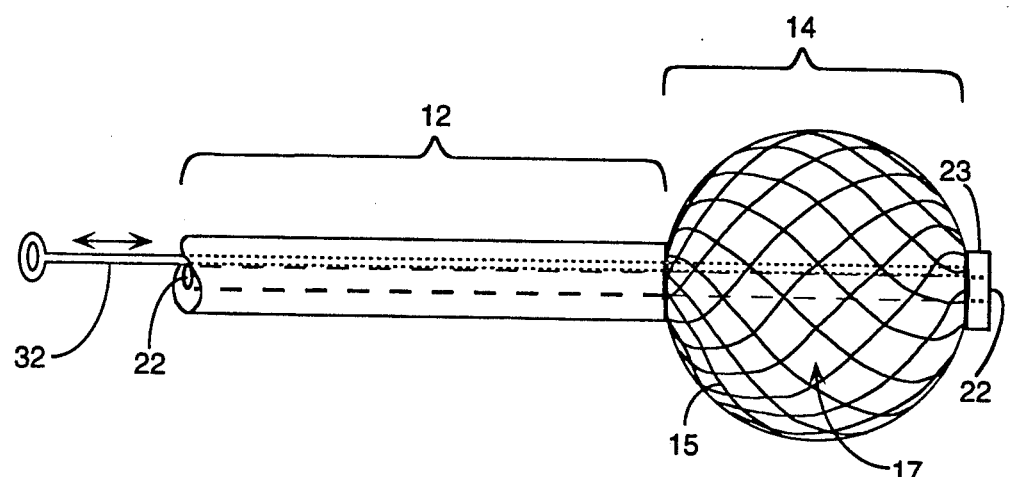
FIG. 4 is a view of the mapping catheter with the deformable lead body in the expanded position.

FIG. 4 shows that the wire stylet 32 is attached to the distal braid ring 23 and positioned in the lumen 22. Traction applied to the distal braid ring 23 by relative motion of the stylet 32 with respect to the lead body 12 causes the braid 15 to change shape. In general, traction causes the braid 15 to move from a generally cylindrical form seen in FIG. 3 to a generally spherical form seen best in FIG. 1 and FIG. 4.

The preferred technique is to provide a stylet 32 which can be used to pull the braid 15 which will deploy the electrode array 16. However, other techniques may be used as well including an optional balloon 17 (FIG. 2) which could be inflated under the electrode array 16 thereby causing the spherical deployment of the array 16. Modification of the braid 15 can be used to control the final shape of the array 16. For example an asymmetrical braid pattern using differing diameter wires within the braid can preferentially alter the shape of the array. The most important property of the geometric shape is that it spaces the electrode sites relatively far apart and that the shape be predictable with a high degree of accuracy.

Figure 5:
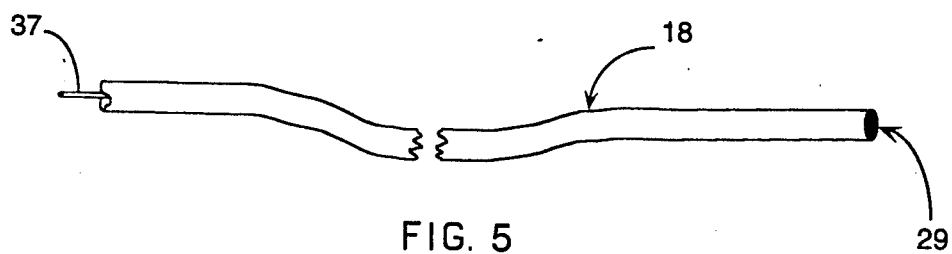
FIG. 5 is a view of the reference catheter.

FIG. 5 shows a first embodiment of the reference catheter 18 where the distal electrode assembly 29 is blunt and may be used to make a surface measurement against the endocardial surface. In this version of the catheter assembly the wire 37 (FIG. 1) communicates to the distal tip electrode and this wire may be terminated in the connector 19.

Figure 6:
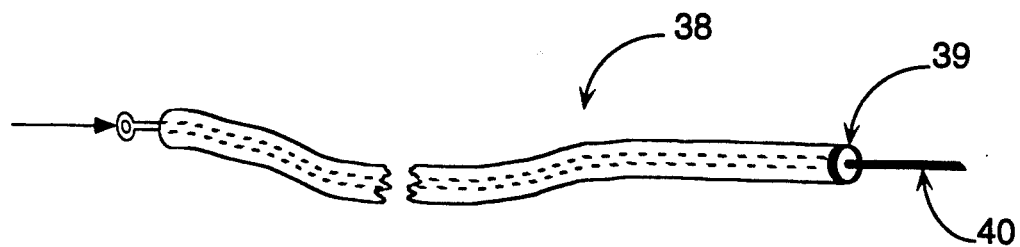
FIG. 6 is a side view of an alternate reference catheter.

FIG. 6 shows an alternate reference catheter 38 which is preferred if both surface and/or subsurface measurements of the potential proximate the endocardial surface are desired. This catheter 38 includes both a ring electrode 39 and an extendable intramural electrode body 40.

Figure 7:
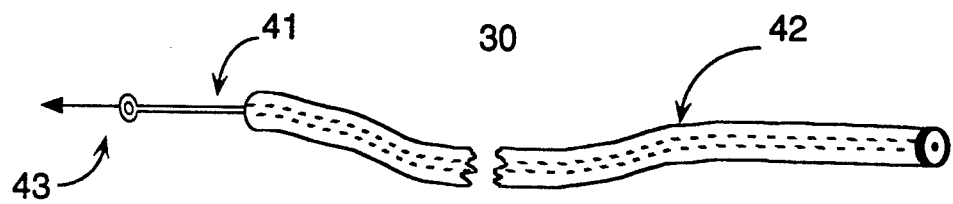
FIG. 7 is a side view of an alternate reference catheter.

FIG. 7 illustrates the preferred use of an intramural electrode stylet 41 to retract the sharp intramural electrode body 40 into the reference catheter lead body 42. Motion of the intramural electrode body 40 into the lead body 42 is shown by arrow 43.

Figure 8:
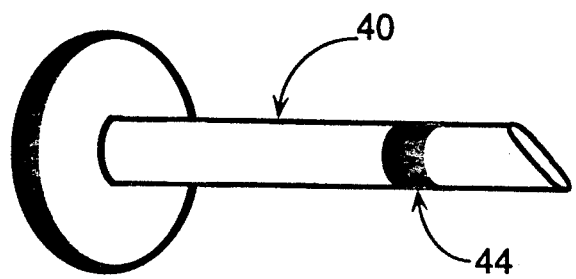
FIG. 8 is a perspective view of an alternate distal tip.

FIG. 8 shows the location of the intramural electrode site 44 on the electrode body 40. It is desirable to use a relatively small electrode site to permit localization of the intramural electrical activity.

The array catheter 11 may be made by any of a variety of techniques. In one method of manufacture, the braid 15 of insulated wires 33,34,35,36 can be encapsulated into a plastic material to form the flexible lead body 12. This plastic material can be any of various biocompatible compounds with polyurethane being preferred. The encapsulation material for the flexible lead body 12 is selected in part for its ability to be selectively removed to expose the insulated braid 15 to form the deformable lead body 14. The use of a braid 15 rather than a spiral wrap, axial wrap, or other configuration inherently strengthens and supports the electrodes due to the interlocking nature of the braid. This interlocking braid 15 also insures that, as the electrode array 16 deploys, it does so with predictable dimensional control. This braid 15 structure also supports the array catheter 11 and provides for the structural integrity of the array catheter 11 where the encapsulating material has been removed.

To form the deformable lead body 14 at the distal end of the array catheter 11, the encapsulating material can be removed by known techniques. In a preferred embodiment this removal is accomplished by mechanical removal of the encapsulating material by grinding or the like. It is also possible to remove the material with a solvent. If the encapsulating material is polyurethane, tetrahydrofuran or cyclohexanone can be used as a solvent. In some embodiments the encapsulating material is not removed from the extreme distal tip to provide enhanced mechanical integrity forming a distal braid ring 23.

With the insulated braid 15 exposed, to form the deformable lead body 14 the electrodes sites can be formed by removing the insulation over the conductor in selected areas. Known techniques would involve mechanical, thermal or chemical removal of the insulation followed by identification of the appropriate conducting wire at the proximal connector 19. This method makes it difficult to have the orientation of the proximal conductors in a predictable repeatable manner. Color coding of the insulation to enable selection of the conductor/electrode is possible but is also difficult when large numbers of electrodes are required. Therefore it is preferred to select and form the electrode array through the use of high voltage electricity. By applying high voltage electricity (typically 1-3 KV) to the proximal end of the conductor and detecting this energy through the insulation it is possible to facilitate the creation of the electrode on a known conductor at a desired location. After localization, the electrode site can be created by removing insulation using standard means.

Modifications can be made to this mapping catheter assembly without departing from the teachings of the present invention. Accordingly the scope of the invention is only to be limited only by the accompanying claims.

We claim:

1. A mapping catheter for use in mapping cardiac electrical potentials of a patient's heart comprising:
    a set of electrodes;
    first positioning means coupled to said set of electrodes for spacing a portion of said set of electrodes, defined as a first subset of electrodes, apart from and not in contact with a surface of said patient's heart;
    second positioning means coupled to said set of electrodes for placing a second predetermined subset of said set of electrodes into contact with a surface of said patient's heart, said second predetermined subset being different from said first subset; and
    means for excluding blood from an interior of said spaced portion of said set of electrodes.

2. The apparatus of claim 1 further comprising:
    third positioning means coupled to said set of electrodes for placing a third predetermined subset of said electrodes into a position beneath a surface of said patient's heart.

3. The apparatus of claim 1 wherein said set of electrodes exceeds twelve electrodes.

4. The apparatus of claim 1 wherein said first subset of electrodes exceeds one electrode.

5. The apparatus of claim 1 wherein said second subset is at least one electrode.

6. The apparatus of claim 1 wherein said first positioning means is substantially spherical in shape.

7. The apparatus of claim 1 wherein said second positioning means is a substantially linear shape.

8. A catheter assembly for mapping the interior of a patient's heart comprising:
    a first set of electrode sites defining a first electrode array;
    said electrode array adapted to be positioned within said patient's heart with a substantial number of said electrodes not in contact with said heart;
    a second set of electrode sites adapted to be located in contact with said patient's heart, said second set of electrode sites being different from said first set of electrode sites; and
    means for excluding blood from an interior of said electrode array.

9. A catheter assembly for mapping the electrical potential of the interior of a heart chamber of a patient's heart, comprising:
    a flexible lead body, connected to a deformable lead body, said flexible lead body and said deformable lead body having a lumen;
    said deformable lead body deformable to a first collapsed position wherein said deformable lead body has a substantially cylindrical shape and, said deformable lead body deformable to a second expanded position wherein said deformable lead body has a substantially spherical shape;
    an electrode array having a plurality of electrode sites located proximate said deformable lead body, wherein said electrode sites form a spherical array of electrode sites when said deformable lead body is in said second expanded position;
    a reference catheter having a tip electrode assembly;
    said reference catheter being located in said lumen and supported for relative motion with respect to said electrode array such that said tip electrode assembly may be placed into contact with said patient's heart when said array is in said heart chamber.

10. The catheter assembly of claim 9 further comprising:
    means for excluding blood from the interior of said deformable lead body when said deformable lead body is in said second expanded position.

11. The catheter assembly of claim 9 wherein said flexible lead body comprises a braid of insulated wires incorporated into a polymeric sheath.

12. A method of forming a catheter comprising the steps of:
    a) forming a collection of insulated wires each having an interior conductor, and each having an exterior insulation coating;
    b) braiding the wires formed in step a) forming braided structure having a central lumen;
    c) incorporating the braided structure in a polymeric material forming a flexible lead body;
    d) removing said polymeric material from a portion of said flexible lead body exposing said braid of insulated wires forming a deformable lead body;
    e) removing insulation from selected locations on selected insulated wires to form electrode sites on said deformable lead body.

* * * * *

UNITED STATES PATENT AND TRADEMARK OFFICE
CERTIFICATE OF CORRECTION

PATENT NO. : 5,311,866

DATED : May 17, 1994

INVENTOR(S) : Kagan et al.

It is certified that error appears in the above-identified patent and that said Letters Patent is hereby corrected as shown below:

In column 1, line 6, please delete the words "patent application" and insert therefor --Patent Application--

In column 3, line 13, before the word "construction", please delete "o" and insert therefor --of--

Signed and Sealed this

Fourteenth Day of February, 1995

Attest:

BRUCE LEHMAN

*Attesting Officer*     *Commissioner of Patents and Trademarks*